United States Patent [19]

Saville

[11] Plant 4,811

[45] Jan. 26, 1982

[54] ROSE PLANT

[75] Inventor: F. Harmon Saville, Rowley, Mass.

[73] Assignee: Nor'East Miniature Roses, Inc., Rowley, Mass.

[21] Appl. No.: 189,752

[22] Filed: Sep. 22, 1980

[51] Int. Cl.[3] ..... A01H 5/00

[52] U.S. Cl. ..... Plt./10

[58] Field of Search ..... Plt./10

*Primary Examiner*—James R. Feyrer
*Attorney, Agent, or Firm*—Vincent G. Gioia

[57] ABSTRACT

A new high centered red miniature rose which develops into Indian Lake red tonality upon aging.

1 Drawing Figure

The present invention relates to a new and distinct variety of rose plant of the miniature rose class, which was originated by my crossing as seed parent the rose known as "Sheri Anne" and the rose known as "Tamango" as pollen parent.

Among the novel characteristics possessed by this new variety which distinguish it from its parents and all other varieties of which I am aware are relatively large hybrid tea-like flowers of red coloring and good form with heavy but considerably variable petalage. As the flowers age they take on a purplish cast but remain vibrant. Asexual reproduction by budding of the new variety as performed in Essex County, Mass., shows that the foregoing and other distinguishing characteristics come true to form and are established and transmitted through succeeding propagations.

The new and improved rose variety which I have developed is a fine miniature rose beginning as a currant red bud and then tending toward vibrant magenta-like coloring upon aging. Like hybrid teas, the flowers tend to be singly-borne and high centered. The changing colors upon aging result in an eye-catching plant for display with varying but similar red and magenta-like tones often visible at the same time.

The accompanying drawing shows typical specimens of the vegetative growth and flowers of the new variety in different stages of development and as depicted in color as nearly true as it is reasonably possible to make the same in color illustration of this character.

The following is a detailed description of my new variety, with color terminology in accordance with the Royal Horticultural Society Color Chart (RHSCC). The terminology used in color description herein refers to plate numbers in the aforementioned color chart, e.g., "47A" is plate 47A of the Royal Horticultural Society Color Chart.

Parentage: Seedling.
*Seed parent.*—"Sheri Anne".
*Pollen parent.*—"Tamango".
Class: Miniature.

The following observations are made of specimens grown in Essex County, Mass., during the month of July.

FLOWER

Blooming habit: Recurrent, near continuous.

A. Bud:
(1) *Size.*—Medium.

(2) *Form.*—Ovate.
(3) *Color.*—When sepals first divide — 47A. As petals begin to unfurl color tends toward 53A, B bud takes on some 57D.
(4) *Sepals.*—Smooth, longer than bud.
(5) *Peduncle.*—Length — about ¾ to 1 inch. Aspect — straight. Strength — erect, strong. Color — 144B.

B. Bloom:
(1) *Size.*—Average size when fully expanded — about 1½ to 2 inches.
(2) *Borne.*—Primarily singly.
(3) *Form.*—High centered at first, becoming flat upon opening, petals remaining at first loosely rolled outward.
(4) *Petalage.*—Number of petals under normal conditions — about 40 to 65.
(5) *Color.*—Currant red buds seen only immediately after sepals divide, unfurl to 53A, B. As flower opens red purple coloring increases and at ⅓ to ½ open predominant color is near to 57D bud as fully open bloom color tends toward Indian Lake 58A not quite, but similar to, a vibrant magenta tonality from a distance.

C. Petals:
(1) *Texture.*—Thick.
(2) *Appearance.*—Inside — satiny; outside — satiny.
(3) *Form.*—Fan shaped but quilling to a starlike point.
(4) *Arrangement.*—Shingle-like.
(5) *Petaloids in center.*—Few.
(6) *Persistence.*—Drop cleanly.
(7) *Fragrance.*—Slight.
(8) *Lasting quality.*—Long on plant and as cut flower.

REPRODUCTIVE ORGANS

A. Stamens, filaments and anthers:
(1) *Arrangement.*—Stamens regularly arranged around styles.
(2) *Color.*—Orange yellow.

B. Pollen: Color — 66C, edged 24B.
C. Styles: Color — 57A.
D. Stigmas: Color — 57C.
E. Hips: Globular, medium size, Spanish orange color when mature, seeds do not protrude.

PLANT

A. Form: Spreading.
B. Growth: Very vigorous, free branching.

*Height attained.*—12 to 15 inches.

C. Foliage: Compound 5 to 7 leaflet leaves.

(1) *Size.*—Medium.

(2) *Quantity.*—Abundant.

(3) *Color.*—Upper side — 137A. Under side — 147C.

(4) *Shape.*—Long, ovoid.

(5) *Texture.*—Upper side — normal. Under side — matte.

(6) *Edge.*—Serrated.

(7) *Serration.*—Normal.

(8) *Leaf stem.*—Color — near to 137C. Under side — near to 147C.

(9) *Stipules.*—Long and smooth.

(10) *Resistance to disease.*—Blackspot — average. Mildew — average.

D. Wood:

(1) *New wood.*—Color — near 144A. Bark — smooth.

(2) *Old wood.*—Color — near to 143B. Bark — smooth.

E. Thorns:

(1) *Thorns.*—Quantity—few. On laterals from stalk — few. Form — short, straight, pointed. Length — short. Color (when young) — 181D. Position — irregular.

(2) *Prickles.*—None.

F. Winter hardiness: Needs some protection in extreme climate.

I claim:

1. A new and distinct variety of rose plant of the miniature class, substantially as shown and described, characterized particularly by red buds becoming reddish purple blooms borne primarily singly developing into Indian Lake red upon aging.

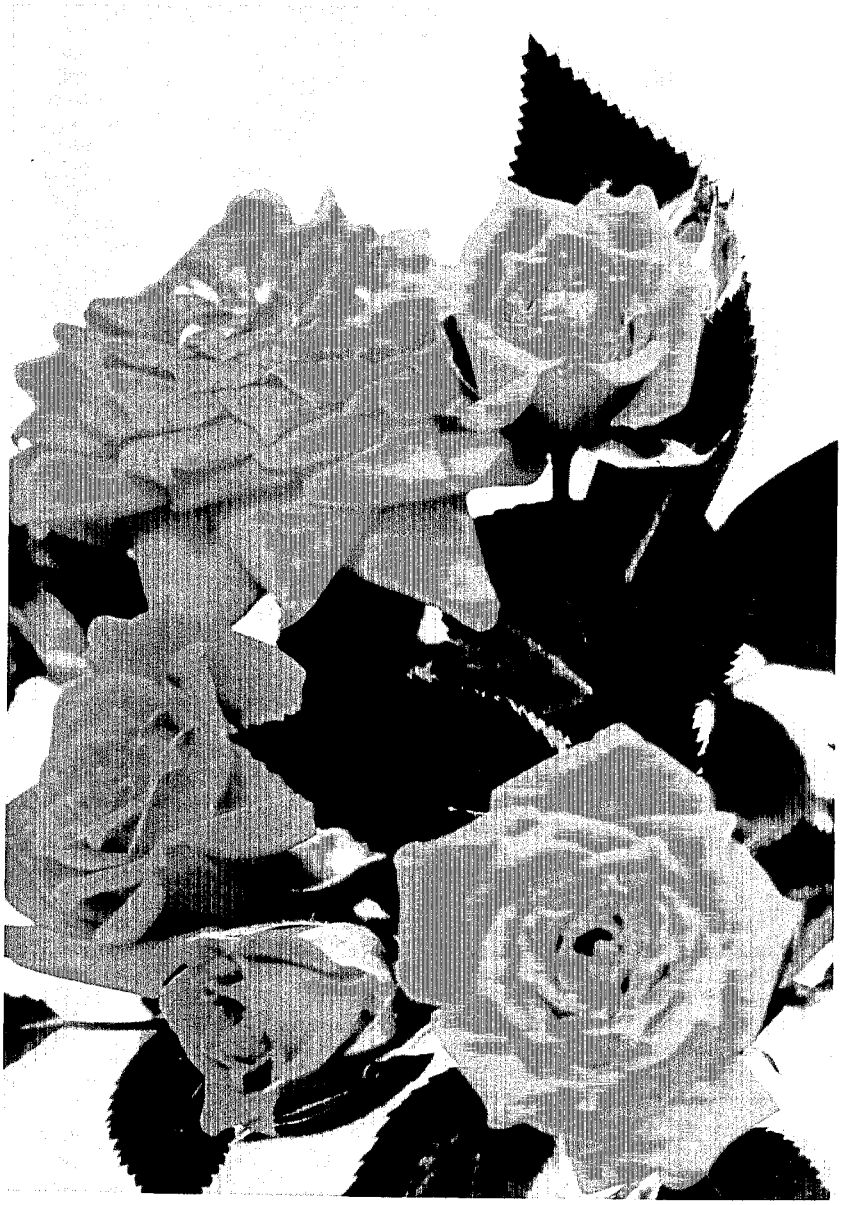

* * * * *